(12) United States Patent
Hayashi

(10) Patent No.: US 9,097,635 B2
(45) Date of Patent: *Aug. 4, 2015

(54) PROPERTY MEASUREMENT APPARATUS AND PROPERTY MEASUREMENT METHOD

(75) Inventor: Yoshihito Hayashi, Chiba (JP)

(73) Assignee: Sony Corporation, Tokyo (JP)

( * ) Notice: Subject to any disclaimer, the term of this patent is extended or adjusted under 35 U.S.C. 154(b) by 566 days.

This patent is subject to a terminal disclaimer.

(21) Appl. No.: 13/371,881

(22) Filed: Feb. 13, 2012

(65) Prior Publication Data

US 2012/0137753 A1 Jun. 7, 2012

Related U.S. Application Data

(63) Continuation of application No. 12/472,630, filed on May 27, 2009, now Pat. No. 8,132,446.

(30) Foreign Application Priority Data

May 29, 2008 (JP) ................................. 2008-140530

(51) Int. Cl.
*G01N 11/14* (2006.01)
*G01N 11/16* (2006.01)
*G01N 11/00* (2006.01)

(52) U.S. Cl.
CPC ............ *G01N 11/142* (2013.01); *G01N 11/165* (2013.01); *G01N 2011/0066* (2013.01)

(58) Field of Classification Search
CPC ...................................................... G01N 11/14
USPC ............. 73/54.41, 54.28, 32 A, 54.01, 290 V, 73/54.24, 64.53, 54.02, 54.37–54.39, 574, 73/575

See application file for complete search history.

(56) References Cited

U.S. PATENT DOCUMENTS

| | | | | |
|---|---|---|---|---|
| 4,779,452 A * | 10/1988 | Cohen-Tenoudji et al. | . | 73/54.41 |
| 5,417,314 A * | 5/1995 | Sproston et al. | ........... | 188/267.1 |
| 5,571,952 A * | 11/1996 | Kauzlarich | .................. | 73/54.24 |
| 5,764,068 A * | 6/1998 | Katz et al. | ...................... | 324/727 |
| 5,983,727 A * | 11/1999 | Wellman et al. | ................. | 73/724 |
| 6,167,752 B1 * | 1/2001 | Raffer | .......................... | 73/54.28 |
| 6,252,398 B1 * | 6/2001 | Goldfine et al. | .............. | 324/239 |
| 6,499,336 B1 * | 12/2002 | Raffer | .......................... | 73/54.28 |
| 6,571,610 B1 * | 6/2003 | Raffer | .......................... | 73/54.35 |
| 7,146,849 B2 * | 12/2006 | Care et al. | .......................... | 73/40 |
| 7,275,419 B2 * | 10/2007 | Raffer | .......................... | 73/54.28 |
| 7,398,685 B2 * | 7/2008 | Itoh et al. | ......................... | 73/599 |

(Continued)

FOREIGN PATENT DOCUMENTS

| | | |
|---|---|---|
| JP | 4-177145 A | 6/1992 |
| JP | 06-109710 | 4/1994 |
| JP | 11-194346 | 7/1999 |
| JP | 2000-180486 A | 6/2000 |
| JP | 2001-242067 A | 9/2001 |

(Continued)

*Primary Examiner* — Hezron E Williams
*Assistant Examiner* — Hoang Nguyen
(74) *Attorney, Agent, or Firm* — Wolf, Greenfield & Sacks, P.C.

(57) ABSTRACT

Disclosed herein is a property measurement apparatus including: a first plate installed in a state of being rotatable and/or vibratable; and a second plate placed to face the first plate and provided with an impedance measurement section, wherein a stress caused by a distortion generated by rotating or vibrating the first plate to serve as a distortion given to a sample provided in a gap between the first and second plates is measured, and at the same time, the impedance measurement section measures the impedance of the sample.

18 Claims, 3 Drawing Sheets

(56) References Cited

U.S. PATENT DOCUMENTS

| | | |
|---|---|---|
| 7,694,551 B2 * | 4/2010 | Jakoby ........................ 73/54.26 |
| 7,804,308 B2 | 9/2010 | Podhajsky et al. |
| 8,368,410 B2 * | 2/2013 | Hayashi et al. ............... 324/693 |
| 2001/0054894 A1 * | 12/2001 | Goldfine et al. ......... 324/207.17 |
| 2005/0168663 A1 | 8/2005 | Miyachi et al. ................. 349/24 |
| 2009/0039900 A1 * | 2/2009 | Podhajsky et al. ............ 324/663 |
| 2010/0136606 A1 | 6/2010 | Katsumoto et al. |

FOREIGN PATENT DOCUMENTS

| | | |
|---|---|---|
| JP | 2002-082042 A | 3/2002 |
| JP | 2003-509692 A | 3/2003 |
| JP | 2004-239788 A | 8/2004 |
| JP | 2006-214763 A | 8/2006 |
| JP | 2006-220646 A | 8/2006 |
| JP | 2006-262014 A | 9/2006 |
| JP | 2009-068864 A | 4/2009 |

* cited by examiner

PROPERTY MEASUREMENT APPARATUS AND PROPERTY MEASUREMENT METHOD

CROSS REFERENCES TO RELATED APPLICATIONS

This application is a continuation of U.S. patent application Ser. No. 12/472,630, titled "PROPERTY MEASUREMENT APPARATUS AND PROPERTY MEASUREMENT METHOD," filed on May 27, 2009, which claims the benefit under 35 U.S.C. §119 of Japanese Patent Application JP 2008-140530, filed on May 29, 2008. The contents of these applications are hereby incorporated by reference in their entireties.

BACKGROUND OF THE INVENTION

1. Field of the Invention

In general, embodiments of the present invention relates to a property measurement apparatus for measuring a stress which is generated in a sample when a distortion is given to the sample and measuring the impedance of the sample and relates to a property measurement method to be adopted by the property measurement apparatus. More particularly, the embodiments of the present invention relates to a technology for measuring both the dynamic viscoelasticity and dielectric characteristic of a sample at the same time in one measurement.

2. Description of the Related Art

In the past, a rotary rheometer has been used widely for measuring dynamic viscoelasticity. In general, a rotary rheometer has a configuration in which a sample is sandwiched by a planar lower plate fixed on the rheometer apparatus and a conical or planar upper plate having an upper surface linked to a bearing by a shaft. In such a configuration, the upper plate is rotated or vibrated in order to give a distortion to the sample and a stress caused by the distortion is then measured.

At that time, the frequency of the rotation or the vibration applied to the sample can be changed in order to obtain dynamic information. Then, the viscoelasticity of the sample is found on the basis of the dynamic information. In the rheometer having such a configuration, an air bearing can be used as the bearing in order to allow an infinitesimal stress to be detected and allow a sample having a low degree of viscosity to be measured effectively.

In place of the configuration in which a sample is sandwiched by the lower and upper plates as described above, the rotary rheometer may have a configuration in which an outer cylinder and an inner cylinder or an inner cylindrical column are provided concentrically, and a sample is injected into a gap between the outer cylinder and the inner cylinder or the inner cylindrical column, being subjected to measurements. In the case of the rheometer having such a configuration, the inner cylinder (or the inner cylindrical column) or the outer cylinder is rotated or vibrated and a stress caused by the rotation or the vibration is detected.

In the rheometer having the configuration including a pair of lower and upper plates as described above, the configuration of sandwiching a sample between the plates is regarded as a capacitor. Thus, by applying a voltage between the plates, the dielectric response of the sample can be observed. In this case, however, physical contact of a conductor with the upper plate is required in a form as electrical contact. As described above, the upper plate needs to be rotated or vibrated in order to measure the dynamic viscoelasticity of the sample. To put it concretely, when measuring both the dynamic viscoelasticity and dielectric characteristic of a sample by making use of the existing property measurement apparatus, at least, two surfaces coming into contact with the sample are manufactured from a conductor material and, in addition, a metallic clip or the like is brought into contact with the rotation shaft in order to establish electrical contact with the two surfaces.

In addition, in the past, there has also been proposed a method for finding the viscosity coefficient and dielectric constant of liquid part of a subject of measurement from values obtained as a result of measurements of propagation-speed and propagation-loss differences between elastic surface waves which are input when comb-shaped electrodes forming elastic surface propagation lines are submerged into the liquid part of the subject of measurement. For more information on the proposed method, the reader is suggested to refer to Japanese Patent Laid-Open No. Hei 6-109710 (hereinafter referred to as Patent Document 1) and Japanese Patent Laid-Open No. Hei 6-194346 (hereinafter referred to as Patent Document 2).

SUMMARY OF THE INVENTION

In the case of the method for measuring a dielectric characteristic of a sample by bringing the metallic clip into contact with the rotation shaft of the rotary rheometer, however, when a sample with a small viscosity coefficient is measured, frictions between the metallic clip and the rotation shaft become predominant so that the dynamic response of the sample can no longer be observed. As a result, there is raised a problem that the precision of the measurement of the dynamic viscoelasticity deteriorates. In addition, also in the measurement of a dielectric characteristic, the goodness and badness of electric contact with the metallic clip varies every second due to the movement of the rotation shaft, and the variations in goodness and badness become large noises. As a result, there is raised a problem that the dielectric response of the sample cannot be evaluated correctly. That is to say, the method of bringing a member into contact with the rotation shaft and/or the upper plate in order to assure electrical contacts with the rotation shaft and/or the upper plate undesirably introduces large errors to both the dynamic measurement and the electric measurement.

It is to be noted that, in addition to the method of bringing the metallic clip into contact with the rotation shaft and/or the upper plate in order to assure electrical contacts with the rotation shaft and/or the upper plate, there is also a method of making use of mercury for the bearing. However, this method is not capable of measuring an extremely small torque by making use of an air bearing. Thus, there is a problem that applications of this method are very limited. In addition, since this method makes use of mercury, from the safety point of view, this method is not desirable.

On the other hand, measurement apparatus described in Patent Documents 1 and 2 are used for measuring the viscosity coefficient, dielectric constant and specific electric conductivity of a sample from results of acoustic impedance measurements on the basis of a particular model. Since the viscosity coefficient, the dielectric constant and the specific electric conductivity are not measured directly, however, there is a problem that the reliability of the measured value of each of the viscosity coefficient, the dielectric constant and the specific electric conductivity is poor in comparison with values obtained as results of direct measurements. In addition, the configuration of each of the measurement apparatus described in Patent Documents 1 and 2 raises a problem that the apparatus are not capable of measuring the dynamic viscoelasticity by varying the measurement frequency. In addition, each of the measurement apparatus described in Patent Documents 1 and 2 has a structure designed by not assuming implementation of a high-frequency transmission line. Thus, each of the measurement apparatus described in Patent Documents 1 and 2 raises a problem that it is impossible to measure the dielectric constant and the specific electric conductivity with a high degree of precision in a high frequency range such as the range of frequencies not lower than 1 MHz in particular.

As described above, the existing measurement apparatus and the existing measurement method are not capable of measuring both the dynamic viscoelasticity and dielectric characteristic of a sample having a small viscosity coefficient in one measurement at the same time with a high degree of precision. Typical examples of the sample having a small viscosity coefficient are a sample made of a liquid-state material and a sample at an initial stage of a gelatification process. In addition, in the case of a sample having a large viscosity coefficient, the precision of the measurement needs to be improved by suppressing noises.

Addressing the problems described above, inventors of the present invention have innovated a property measurement apparatus capable of measuring both the dynamic viscoelasticity and dielectric characteristic of a sample in one measurement at the same time with a high degree of precision and innovated a property measurement method to be adopted in the property measurement apparatus.

A property measurement apparatus according to an embodiment of the present invention employs: a first plate installed in a state of being rotatable and/or vibratable; and a second plate placed to face the first plate and provided with an impedance measurement section, wherein: a stress caused by a distortion generated by rotating or vibrating the first plate to serve as a distortion given to a sample provided in a gap between the first and second plates is measured; and at the same time, the impedance measurement section measures the impedance of the sample.

In the property measurement apparatus according to the embodiment of the present invention, the impedance measurement section for measuring the impedance of a sample is provided on the second plate instead of providing the impedance measurement section on the first plate which is linked to a rotation shaft. Thus, the rotation shaft does not have an effect from the impedance measurement on the dynamic response of the sample.

In addition, the impedance measurement section employed in the property measurement apparatus according to an embodiment of the present invention has a configuration employing at least: an insulation layer; a pair of conductive layers facing each other to sandwich the insulation layer and each functioning as a high-frequency transmission lines and a layer breaking gap which is formed on the conductive layer on the side close to the first plate to break the conductive layer and allows a portion of the sample to be introduced thereto, wherein: a voltage is applied between the conductive layers; and an impedance which may change due to introduction of the sample to the layer breaking gap is measured.

As an alternative, the impedance measurement section employed in the property measurement apparatus according to an embodiment of the present invention has a configuration employing at least: an insulation layer; a pair of comb-shaped electrodes formed in a state of being engaged with each other and separated away from the surface of the insulation layer by a fixed gap, wherein: a voltage is applied between the comb-shaped electrodes; and an impedance which may change due to introduction of the sample to a gap between a specific one of the comb-shaped electrodes and the other one of the comb-shaped electrodes is measured.

In addition, any one of the property measurement apparatus according to the embodiment of the present invention may have an analysis section for computing: a dynamic viscoelasticity of the sample on the basis of the measured stress; and a dielectric characteristic of the sample on the basis of the measured impedance.

The sample has at least one of types such as a liquid, a suspension liquid and a gel-state substance.

A property measurement method provided in accordance with an embodiment of the present invention as a property measurement method to be adopted in a property measurement apparatus employing: a first plate installed in a state of being rotatable and/or vibratable; and a second plate placed to face the first plate and provided with an impedance measurement section, whereby a stress caused by a distortion generated by rotating or vibrating the first plate to serve as a distortion given to a sample provided in a gap between the first and second plates is measured, and at the same time, the impedance measurement section measures the impedance of the sample.

In the property measurement apparatus according to the embodiment of the present invention, the impedance measurement section for measuring the impedance of a sample is provided in the second plate instead of providing the impedance measurement section in the first plate which is linked to a rotation shaft. Thus, even if a sample having a small viscosity coefficient or a sample having a large viscosity coefficient is used as a subject of measurement, both the dynamic viscoelasticity and dielectric characteristic of the sample can be measured in one measurement at the same time with a high degree of precision. A typical example of the sample having a small viscosity coefficient is a liquid whereas a typical example of the sample having a large viscosity coefficient is a gel-state substance.

BRIEF DESCRIPTION OF THE DRAWINGS

These and other features of the embodiments of the present invention will become clear from the following description of the preferred embodiments given with reference to the accompanying diagrams, in which.

DETAILED DESCRIPTION OF THE PREFERRED EMBODIMENTS

Figure 1:
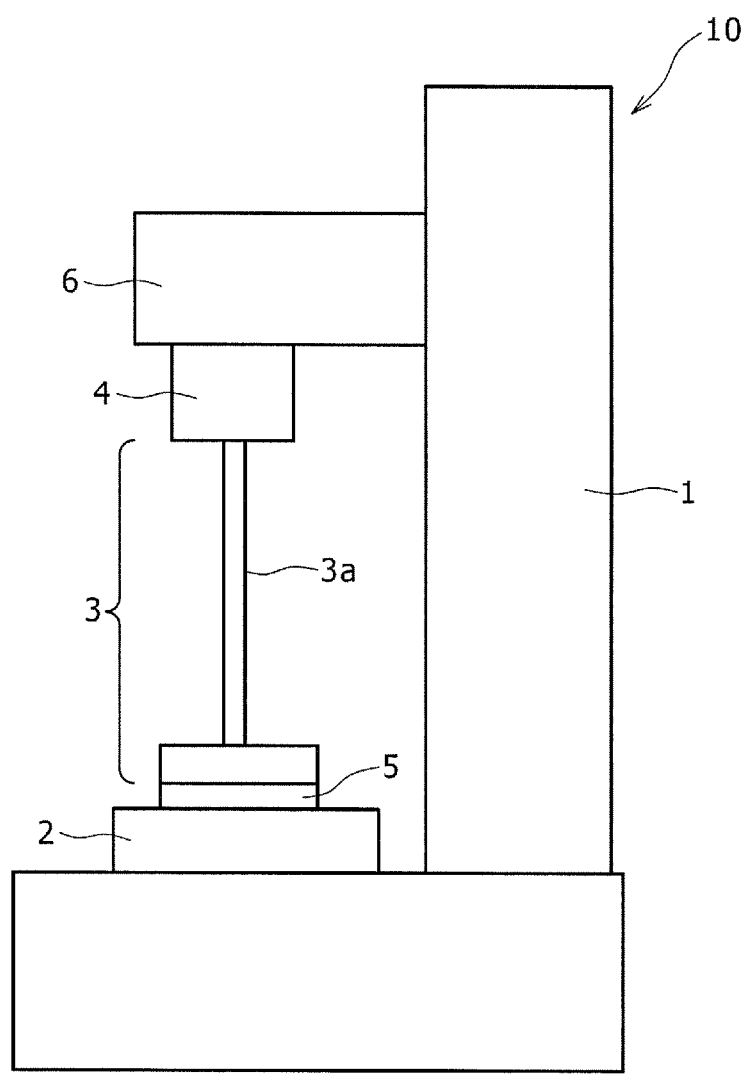
FIG. 1 is a model diagram showing a side view of the configuration of a property measurement apparatus according to a first embodiment of the present invention.

Preferred embodiments of the present invention are explained in detail below by referring to diagrams. It is to be noted, however, that implementations of the present invention are by no means limited to the preferred embodiments.

The property measurement apparatus according to an embodiment of the present invention is an apparatus for measuring the dynamic viscoelasticity and dielectric characteristic of a sample such as a liquid, a suspension liquid or a gel-state substance. The property measurement apparatus employs a rotatable and/or vibratable first plate and a second plate fixed on the main body of the property measurement apparatus in a state of facing the first plate. The sample serving as the subject of measurement is inserted into a gap between the first and second plates. In addition, the property measurement apparatus according to the embodiment of the present invention also has an impedance measurement section provided in the second plate. Thus, while the dynamic viscoelasticity of the sample is being measured, the impedance measurement section is also capable of measuring the dielectric characteristic of the sample at the same time. To put it concretely, the first plate is rotated or vibrated in order to give a distortion to the sample. Then, a stress developed in the sample due to the distortion is measured. At the same time, the impedance measurement section provided in the second plate measures the impedance of the same sample.

The impedance measurement section provided in the second plate does not require that electrical contact with the first plate be assured. In addition, the impedance measurement section can have any configuration as long as the configuration does not have any effect on the measurement of a stress of the sample. To put it concretely, a specific one of the surfaces of the second plate is a surface with which the sample is to be brought into contact. The impedance measurement section has a typical configuration including thin-film electrodes, which each form a micro strip line, on the specific surface of the second plate. In the case of a measurement of the dielectric characteristic at frequencies not exceeding 1 MHz without carrying out the measurement at a higher frequency, each of the electrodes of the impedance measurement section does not have to be the thin-film electrode forming a micro strip line. For example, the electrode of the impedance measurement section can also be another planar electrode which can be used for carrying out the same impedance measurement as the thin-film electrodes each forming a micro strip line. To put it concretely, for example, the impedance measurement section has a typical configuration including comb-shaped planar electrodes created by carrying out a film creation process such as a vapor deposition process or a sputtering process above the specific surface of the second plate, that is, above the surface with which the sample is brought into contact.

As described above, by making use of the second plate fixed on the main body of the property measurement apparatus, the impedance of a sample can be measured. It is thus no longer necessary to bring a member, which is to be used for establishing electrical contact with operating sections such as the first plate and/or a rotation shaft linked to the first plate, into physical contact with the operating sections. As a result, it is possible to substantially improve the precision of a measurement process of measuring both the dynamic viscoelasticity and dielectric characteristic of a sample at the same time. Therefore, it is possible to measure both the dynamic viscoelasticity and dielectric characteristic of a sample in a wide range at the same time with a high degree of precision. The wide range covers samples ranging from a sample having a small viscosity coefficient to a sample having a large viscosity coefficient. A typical example of the sample having a small viscosity coefficient is a liquid whereas a typical example of the sample having a large viscosity coefficient is a gel-state substance.

First of all, the following description explains a property measurement apparatus according to a first embodiment of the present invention. An impedance measurement section formed in a second plate employed in the property measurement apparatus according to the first embodiment has a structure of micro strip lines created on the second plate as will be described later. FIG. 1 is a model diagram showing a side view of the configuration of the property measurement apparatus 10 according to the first embodiment of the present invention. As shown in the model diagram of FIG. 1, the property measurement apparatus 10 according to the first embodiment of the present invention employs a lower plate 2 fixed on the base of an apparatus case 1 which has a shape resembling approximately the L character when the property measurement apparatus 10 is seen from a position on a side of the property measurement apparatus 10. The lower plate 2 includes an impedance measurement section. On the upper portion of the property measurement apparatus 10, a stress measurement head 4 such as an air bearing is attached through a gap adjustment jig 6. An upper plate 3 is fixed on the stress measurement head 4 in a state of being rotatable and/or vibratable. The upper plate 3 is linked to a rotation shaft 3a. The lower plate 2 and the upper plate 3 are respectively the first and second plates mentioned earlier.

The apparatus case 1 of the property measurement apparatus 10 contains sections such as a control section, a display section and an interface. The control section is a section for controlling an operation to rotate and/or vibrate the upper plate 3 and an operation to measure a torque. The display section is a section for displaying information such as the status of the property measurement apparatus 10 and error messages. The interface is a section connected to a computer external to the property measurement apparatus 10.

The upper plate 3 has a portion brought into contact with a sample 5. The portion with which the sample 5 is brought into contact has a commonly known shape such as a disk shape or a conical shape. The commonly known shape of the portion can be properly selected in accordance with the sample 5 serving as a subject of measurement.

The gap adjustment jig 6 has a configuration which allows the gap adjustment jig 6 to be sled in the vertical direction. By changing the vertical-direction position of the gap adjustment jig 6, a gap between the upper plate 3 and a lower plate 2 can be adjusted. When the sample 5 is inserted into the gap between the upper plate 3 and the lower plate 2 or when the sample 5 is removed from the gap for example, the gap adjustment jig 6 is moved in the upward direction in order to increase the height of the gap. By increasing the height of the gap between the upper plate 3 and the lower plate 2, the work to insert the sample 5 into the gap or remove the sample 5 from the gap can be carried out with ease. In addition, the height of the gap between the upper plate 3 and the lower plate 2 is adjusted in accordance with the thickness of the sample 5 serving as a subject of measurement.

Figure 2A:
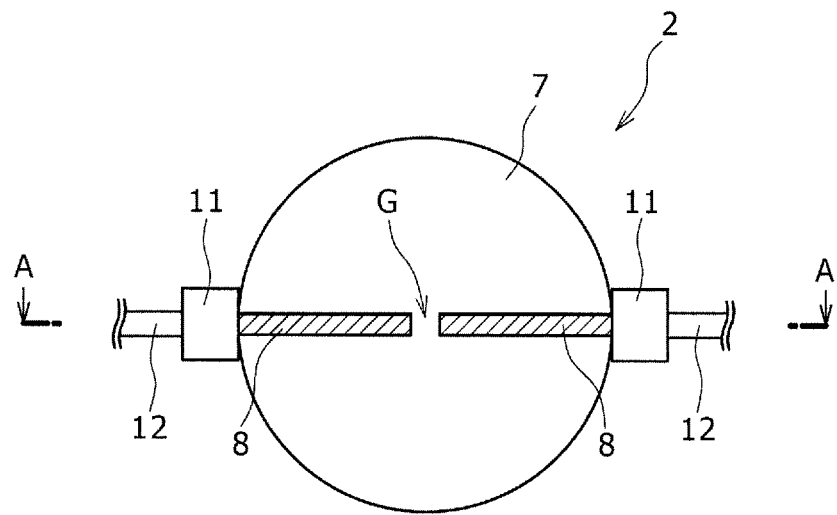
FIG. 2A is a diagram showing the top view of the impedance measurement section of the lower plate employed in the property measurement apparatus according to the first embodiment of the present invention.
Figure 2B:
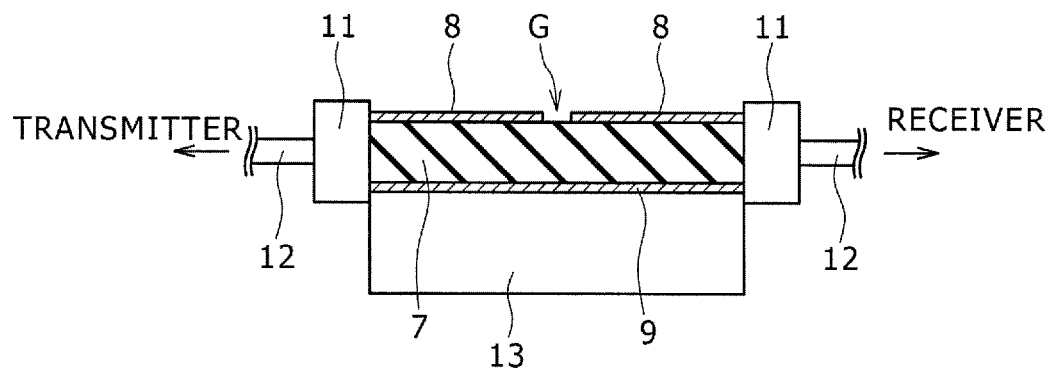
FIG. 2B is a diagram showing the cross section along an A-A line shown in the top-view diagram of FIG. 2A.

The lower plate 2 has a contact surface with which the sample 5 is brought into contact. On the contact surface, micro strip lines including a layer breaking gap having an infinitesimal size is created. FIG. 2A is a diagram showing the top view of the impedance measurement section of the lower plate 2 employed in the property measurement apparatus 10 according to the first embodiment of the present invention whereas FIG. 2B is a diagram showing the cross section along an A-A line shown in the top-view diagram of FIG. 2A. As shown in the top-view diagram of FIG. 2A and the cross-sectional diagram of FIG. 2B, the lower plate 2 employed in the property measurement apparatus 10 according to the first embodiment of the present invention includes conductive layers 8 and 9 created on both sides of a base 7 which is made of an insulation material such as alumina. Each of the conductive layers 8 and 9 is made of a conductive material such as gold.

The upper conductive layer 8 is created on the contact surface with which the sample 5 is brought into contact. As shown in the top-view diagram of FIG. 2A, the upper conductive layer 8 is typically created from one edge on the circumference of the circular base 7 to another edge on the same circumference, forming a band-like shape along a diameter of the base 7. The upper conductive layer 8 includes a layer breaking gap G having an infinitesimal size at a position determined in advance. For example, the position determined in advance is the center point of the base 7 employed in the lower plate 2. That is to say, the upper conductive layer 8 is broken by the layer breaking gap G into left and right segments.

On the other hand, the lower conductive layer 9 is created on the surface on the side close to bottom of the apparatus case 1. The lower conductive layer 9 and the upper conductive layer 8 sandwich the base 7. At least, the lower conductive layer 9 faces the upper conductive layer 8 through the base 7. As an alternative, the lower conductive layer 9 is created all over the surface on the side close to the bottom of the apparatus case 1. It is to be noted that each of the upper conductive layer 8 and the lower conductive layer 9 can be created by carrying out a film creation process such as a vapor deposition process or a sputtering process.

As described above, in the property measurement apparatus 10 according to the first embodiment of the present invention, the base 7 is an insulation layer, on both surfaces of which the upper conductive layer 8 and the lower conductive layer 9 are each created to form a high-frequency transmission line. In the lower plate 2 also functioning as an impedance measurement section having the configuration described above, a sample 5 serving as the subject of measurement is introduced to the layer breaking gap G by adoption of a selected method. With the sample 5 introduced to the layer breaking gap G, an electrical signal is transmitted to the conductive layers 8 and 9. By carrying out an analysis determined in advance on the electrical signal, the impedance of the sample 5 can be measured. To be more specific, in the operation to measure the impedance of the sample 5, a transmitter applies a voltage between the conductive layers 8 and 9 whereas an electrical signal passing through the layer breaking gap G is measured by a receiver. During the operation to measure the impedance of the sample 5, the lower conductive layer 9 is connected to the ground.

The characteristic impedance of the transmission line (strip line) having the configuration described above is determined by parameters such as the dielectric constant of the base 7 serving as the foundation, the thickness of the base 7 and the width of the upper conductive layer 8. Normally, a characteristic impedance of 50 ohms is selected. It is to be noted that the thickness and width of the upper conductive layer 8, the width of the layer breaking gap G and the thickness of the lower conductive layer 9 can be properly set in accordance with factors such as the type of the sample 5 and measurement conditions. For example, if the base 7 serving as the foundation has a thickness of 0.635 mm and is made of alumina which has a dielectric constant of 9.7, the upper conductive layer 8 can be made of a conductive material such as gold with a thickness of 2.5 micrometers and a width of 0.64 mm whereas the width of the layer breaking gap G can be set at 500 micrometers.

In particular, in a measurement of the properties of a heterogeneous suspension-liquid sample such as a sample made of a cellular suspension liquid, it is difficult to introduce a sample component such as a cell to the layer breaking gap G if the width of the layer breaking gap G is small. In such a case, the physical property of a sample portion at a location in close proximity to the layer breaking gap G is different from the physical property of the entire sample so that it is feared that the precision of the measurement deteriorates. It is thus desirable to set the width of the layer breaking gap G at a value at least equal to 50 micrometers. If the width of the layer breaking gap G is too large, on the other hand, the magnitude of an electrical signal propagating from the transmitter to the receiver by way of the layer breaking gap G decreases so that the precision of the measurement also deteriorates in some cases. It is thus desirable to set the width of the layer breaking gap G at a value not greater than 1,000 micrometers.

In addition, a pair of adaptors 11 are provided on both sides of the base 7. One of the adaptors 11 is electrically connected to the upper conductive layer 8 whereas the other adaptor 11 is electrically connected to the lower conductive layer 9. Each of the adaptors 11 is thus a conversion interface placed between a coaxial cable 12 and the micro stripe lines. That is to say, each of the adaptors 11 is connected to a coaxial cable 12. One of the coaxial cables 12 is connected to the transmitter whereas the other coaxial cable 12 is connected to the receiver. The lower plate 2 is linked to the bottom of the apparatus case 1 by a fixing jig 13 and the like.

Next, the following description explains a method adopted by the property measurement apparatus 10 having the configuration described above to serve as a method for measuring the dielectric characteristic of a sample 5. In the property measurement apparatus 10, a voltage is applied between the conductive layers 8 and 9 provided on the lower plate 2. Then, an impedance varying due to introduction of the sample 5 to the layer breaking gap G in the impedance measurement section is measured by making use of a measurement instrument such as an impedance analyzer, a network analyzer or a time-domain dielectric spectral instrument. For example, the impedance measurement section is connected to the measurement instrument by the coaxial cables 12 and a step pulse is applied to the micro strip lines. Then, a wave S11 reflected by the layer breaking gap G and a wave S21 passing through the layer breaking gap G are measured. Subsequently, on the basis of data obtained as a result of the measurement, the analysis section (shown in none of the figures) finds a complex dielectric constant $\in^*$ of the sample 5.

The following description explains a typical technique adopted by the analysis section as a method for analyzing the measurement data. The complex dielectric constant $\in^*$ of the sample can be found in accordance with Eq. 1 given below. It is to be noted that, in Eq. 1, reference notation $Z_x$ denotes a complex impedance, reference notation j denotes the imaginary unit, reference notation ω denotes an angular frequency and reference notation $C_1$ denotes a capacitance related to the measurement sensitivity of the base material of the base 7.

$$Z_x = (j\omega \in^* C)^{-1} \quad \text{(Eq. 1)}$$

By the way, each of the reflected wave $V_r$ reflected by the layer breaking gap G created on the impedance measurement section and the transmitted wave $V_t$ passing through the layer breaking gap G is affected by the complex impedance $Z_x$ of the sample 5. Thus, by analyzing the reflected wave $V_r$ and the transmitted wave $V_t$, the complex dielectric constant $\in^*$ of the sample 5 can be found. Concrete methods for finding the complex dielectric constant $\in^*$ of a sample 5 include (a): a direct method, (b): a reflection/transmission combination method and (c): a reference method which are described as follows.

(a): Direct Method

In accordance with the direct method, the complex dielectric constant $\in^*$ of a sample 5 is found from an input wave $V_i$ and the reflected wave $V_r$ or the transmitted wave $V_t$ by making use of either one of Eqs. 2 to 5 given below.

$$\varepsilon^* = \frac{j}{2\omega Z_0 C_1} \times \frac{(1+z_1^{-1})^2}{1+z_1^{-1} - \bar{v}_i/\bar{v}_t} \quad \text{(Eq. 2)}$$

It is to be noted that, in Eq. 2 given above, reference notation $v_i$ denotes an input wave in the frequency domain whereas reference notation $v_t$ denotes a transmitted wave in the frequency domain. The input wave $v_i$ in the frequency domain can be found by applying a Laplace transform process to the input wave $V_i$ in the time domain. By the same token, the transmitted wave $v_t$ in the frequency domain can be found by applying a Laplace transform process to the input wave $V_t$ in the time domain.

$$\varepsilon^* = \frac{j}{2\omega Z_0 C_1} \times (1 + Z_1^{-1}) \times \left(1 - \frac{\bar{v}_i/\bar{v}_r}{1 + z_1^{-1} + z_1^{-1}\bar{v}_i/\bar{v}_r}\right) \quad \text{(Eq. 3)}$$

It is to be noted that, in Eq. 3 given above, reference notation $Z_0$ denotes the characteristic impedance of the micro strip lines. Normally, a characteristic impedance of 50 ohms is selected. By setting $Z_1$ at the infinity, Eqs. 2 and 3 can be simplified into respectively Eqs. 4 and 5 which are given as follows.

$$\varepsilon^* = \frac{j}{2\omega Z_0 C_1} \times \frac{1}{1 - \bar{v}_i/\bar{v}_t} \ (Z_1 \to \infty) \quad \text{(Eq. 4)}$$

$$\varepsilon^* = \frac{j}{2\omega Z_0 C_1} \times (1 - \bar{v}_i/\bar{v}_r) \ (Z_1 \to \infty) \quad \text{(Eq. 5)}$$

(b): Reflection/Transmission Combination Method

In accordance with the reflection/transmission combination method, the complex dielectric constant ∈* of a sample 5 is found from both the reflected wave $V_r$ and the transmitted wave $V_t$ by making use Eq. 6 given as follows.

$$\varepsilon^* = \frac{1}{j\omega Z_0 C_1} \times \frac{2\bar{v}_i \bar{v}_t}{(\bar{v}_i + \bar{v}_r - \bar{v}_t)} \quad \text{(Eq. 6)}$$

It is to be noted that a quantity $Z_1$ used in Eq. 6 can be found in accordance with Eq. 7 given as follows.

$$Z_1 = \frac{\bar{v}_i + \bar{v}_r + \bar{v}_t}{\bar{v}_i - \bar{v}_r - \bar{v}_t} \quad \text{(Eq. 7)}$$

(c): Reference Method

In accordance with the reference method, in order to find the complex dielectric constant ∈* of a sample 5 serving as the subject of measurement, a standard sample having an already known complex dielectric constant ∈* is measured as a reference sample. In this way, the complex dielectric constant ∈* of the sample 5 serving as the subject of measurement can be found with a higher degree of precision. In accordance with the reference method, the complex dielectric constant ∈* of a sample 5 serving as the subject of measurement is found from the complex dielectric constant ∈$_r$* of the standard sample serving as the reference sample, the reflected wave $V_{rr}$ of the reference sample and the transmitted wave $V_{rt}$ of the reference sample by making use of either one of Eqs. 8 to 12 given below.

$$\varepsilon^* = \varepsilon_r^* \times \frac{\lambda_t}{1 + j2\omega Z_0 C_1 (1 - \lambda_t)(1 + Z_1^{-1})^{-1} \varepsilon_r^*} \ (\lambda_t = \bar{v}_i/\bar{v}_{tr}) \quad \text{(Eq. 8)}$$

$$\varepsilon^* = \frac{1}{j2\omega Z_0 C_1} \times (1 + Z_1^{-1}) \times \quad \text{(Eq. 9)}$$

$$\frac{(1+Z_1^{-1})(1-Z_1^{-1})(1-\lambda_r) + j2\omega Z_0 C_1\{1-Z_1^{-1}(1-\lambda_r)\}\varepsilon_r^*}{(1+Z_1^{-1})\{(1-Z_1^{-1})\lambda_r + Z_1^{-1}\} + j2\omega Z_0 C_1 Z_1^{-1}(1-\lambda_r)\varepsilon_r^*} \ (\lambda_r = \bar{v}_r/\bar{v}_{rr})$$

By setting $Z_1$ at the infinity, Eqs. 8 and 9 can be simplified into respectively Eqs. 10 and 11 which are given below. In addition, by taking both Eqs. 8 and 9 into consideration, Eq. 12 given below can be derived.

$$\varepsilon^* = \varepsilon_r^* \times \frac{\lambda_t}{1 + j2\omega Z_0 C_1(1-\lambda_t)\varepsilon_r^*} (Z_1 \to \infty) \quad \text{(Eq. 10)}$$

$$\varepsilon^* = \varepsilon_r^* \times \frac{j}{2\omega Z_0 C_1} \times \{1 - (1 + j2\omega Z_0 C_1 \varepsilon_r^*)\lambda_r^{-1}\}(Z_1 \to \infty) \quad \text{(Eq. 11)}$$

$$\varepsilon^* = \quad \text{(Eq. 12)}$$

$$\varepsilon_r^* \times \frac{(1-\lambda_t \lambda_r) + j(1-\lambda_t)(1-\lambda_r)\left[\omega Z_0 C_1 \varepsilon_r^* \pm j\sqrt{1-\omega^2 Z_0^2 C_1^2 \varepsilon_r^{*2} + j2\omega Z_0 C_1 \varepsilon_r^* \frac{(1-\lambda_t)}{(1-\lambda_r)}}\right]}{(1-\lambda_r) + (1-\lambda_t)(\lambda_r/\lambda_t) + j2\omega Z_0 C_1 \varepsilon_r^*(1-\lambda_t)(1-\lambda_r)}$$

On top of that, by correcting the stray capacitance $C_r$ of the layer breaking gap G, more precise analysis can be carried out. If the stray capacitance $C_r$ can be neglected, a relation between the complex dielectric constant ∈* of a sample 5 and the complex impedance $Z_x$ can be represented by Eq. 1. If the stray capacitance $C_r$ cannot be neglected, however, the complex impedance $Z_x$ of the measurement system is expressed by Eq. 13 given as follows:

$$Z_x = \frac{1}{j\omega(C_1 + C_r)Z_0} \quad \text{(Eq. 13)}$$

By making use of two reference samples of different types, an effective capacitance $C_1$ getting rid of an effect of the stray capacitance $C_r$ can be found from Eq. 14 or 15 given below. It is to be noted that, as explained before, a reference sample is a sample 5 having an already known complex dielectric constant ∈*.

$$C_1 = \frac{1}{2\omega Z_0} \times \frac{(\bar{v}_{r1r} - \bar{v}_{r2r})\bar{v}_i}{j(\varepsilon_{r1}^* - \varepsilon_{r2}^*)(\bar{v}_i - \bar{v}_{r1t})(\bar{v}_i - \bar{v}_{r2t})} \quad \text{(Eq. 14)}$$

$$C_1 = \frac{1}{2\omega Z_0} \times \frac{(\bar{v}_{r1r} - \bar{v}_{r2r})\bar{v}_i}{j(\varepsilon_{r1}^* - \varepsilon_{r2}^*)\bar{v}_{r1r}\bar{v}_{r2r}} \quad \text{(Eq. 15)}$$

It is to be noted that, once the effective capacitance $C_1$, which is a capacitance related to the measurement sensitivity, is determined by making use of Eq. 14 or 15 given above, one of the two reference samples used in Eq. 14 or 15 is utilized as a standard sample having an already known complex dielectric constant ∈* in order to find the complex dielectric constant ∈* of a sample 5 serving as the subject of measurement in accordance with either one of Eqs. 8 to 12 given above.

If the existence of the stray capacitance $C_r$ is taken into consideration, on the other hand, Eq. 6 given before is changed to Eq. 16 given as follows.

$$C_1 \varepsilon^* + C_r = \frac{1}{j\omega Z_0} \times \frac{2\bar{v}_i \bar{v}_t}{(\bar{v}_i + \bar{v}_r - \bar{v}_t)(\bar{v}_i + \bar{v}_r + \bar{v}_t)} \quad \text{(Eq. 16)}$$

As described above, in the case of the property measurement apparatus 10 according to the first embodiment of the present invention, an impedance measurement section is provided in the lower plate 2 fixed on the apparatus case 1 without the need to assure electrical contact with the upper plate 3. Thus, the dielectric constant of a sample 5 can be measured with a high degree of precision even if the sample 5 is in a liquid state. In addition, in the property measurement apparatus 10, the impedance measurement section is configured to have a structure of micro strip lines and, on top of that, the upper conductive layer 8 is formed as a conductive thin film. Thus, it is possible to all but completely get rid of flow disorders caused by the creation of the impedance measurement section in the lower plate 2 to appear as flow disorders of the fluid. As a result, the viscoelasticity and dielectric characteristic of the same sample 5 can be measured at the same time with a high degree of precision.

The existing property measurement apparatus is not capable of measuring the dynamic viscoelasticity and dielectric characteristic of the same sample 5 at the same time with a high degree of precision if the sample 5 is a sample with a small viscosity in particular. In the case of this embodiment, however, it is not necessary to measure the viscoelasticity and dielectric characteristic of a sample 5 in separate measurements. Instead, the dynamic viscoelasticity and dielectric characteristic can be measured in one measurement with a high degree of precision at the same time. However, advantages offered by the first embodiment of the present invention are not limited to a merit that the length of the measurement time can be reduced and a merit that the measurement work can be simplified. This is because the properties of many samples 5, their property changes with the lapse of time and the like are much affected by typically a variety of infinitesimal impurities which are generated by the property of the material used for making a sample introduction section and generated by the measurement system itself. For example, it is known that, in a process of monitoring blood clotting, differences between substances, with which a sample 5 is to be brought in contact, have an effect on the blood-clotting monitoring time.

It is extremely difficult to construct different measurement systems under completely the same conditions to serve as measurement systems for measuring the dynamic viscoelasticity and the dielectric characteristic separately. By making use of the property measurement apparatus 10 according to the first embodiment of the present invention, on the other hand, it is possible to measure the dynamic viscoelasticity and dielectric characteristic of a sample 5 under essentially the same conditions. As a result, it is possible to evaluate for example proper measures for dealing with the dynamic viscoelasticity and dielectric characteristic of a sample 5.

It is to be noted that the method and principle adopted by the property measurement apparatus 10 to measure the dynamic viscoelasticity of a sample 5 are the same as those adopted by generally known property measurement apparatus such as a rotary rheometer. In addition, in the property measurement apparatus 10 according to the first embodiment, the lower plate 2 is fixed on the apparatus case 1 whereas the upper plate 3 is configured to be rotatable and/or vibratable. However, implementations of the present invention are by no means limited to this configuration according to the first embodiment. For example, conversely, the upper plate is fixed on the apparatus case whereas the lower plate is configured to be rotatable and/or vibratable. In this case, the impedance measurement section is moved to the upper plate which is put in a fixed state.

Figure 3:
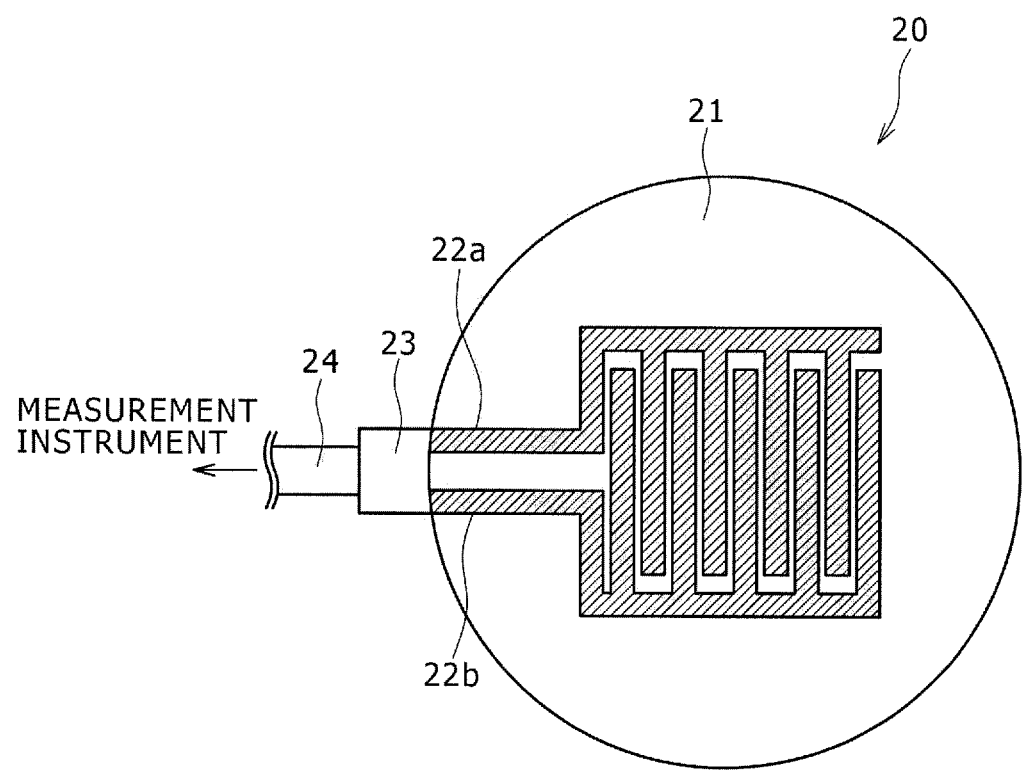
FIG. 3 is a diagram showing the top view of an impedance measurement section embedded in a second plate employed in a property measurement apparatus according to a second embodiment of the present invention.

Next, a property measurement apparatus according to a second embodiment of the present invention is explained as follows. If the frequency band for measuring dielectric characteristic is limited to a band of frequencies not higher than 1 MHz, it is possible to make use of electrodes other than the micro strip lines to serve as the high-frequency transmission lines implemented by the micro strip lines. In a property measurement apparatus according to the second embodiment of the present invention, the impedance measurement section is configured as a pair of electrodes each having a shape resembling a comb such as shown in a diagram of FIG. 3. FIG. 3 is a diagram showing the top view of the impedance measurement section in the second plate 20 employed in the property measurement apparatus according to the second embodiment of the present invention.

As shown in the diagram of FIG. 3, the impedance measurement section in the second plate 20 employed in the property measurement apparatus according to the second embodiment of the present invention is a pair of comb-shaped electrodes 22a and 22b which are engaged with each other. The comb-shaped electrodes 22a and 22b which are separated away by a fixed gap from a specific surface of a base 21 which is made of an insulation material such as alumina and glass. The specific surface of the base 21 is a surface with which the sample 5 is to be brought into contact. By providing a planar electrode structure including the comb-shaped electrodes 22a and 22b engaged with each other in this way, it is possible to increase the strength of an electric field leaking out from the comb-shaped electrodes 22a and 22b to the sample 5. As a result, the sensitivity of the measurement of the impedance of the sample 5 can be improved.

The comb-shaped planar electrodes 22a and 22b can be created by carrying out a film creation process such as a vapor deposition process or a sputtering process at a position above the specific surface of the second plate 20 from a conductive material such as gold with a typical thickness of several micrometers.

In addition, an adaptor 23 is provided on a side surface of a base 21 to serve as a conversion interface placed between a coaxial cable 24 and the comb-shaped planar electrodes 22a and 22b. The end of each of the comb-shaped planar electrodes 22a and 22b is connected to a measurement instrument such as an impedance analyzer through the adaptor 23 and the coaxial cable 24.

In the property measurement apparatus according to the second embodiment of the present invention, a voltage is applied between the comb-shaped planar electrodes 22a and 22b in order to measure an impedance which may vary by introduction of a sample 5 to a gap between the comb-shaped planar electrodes 22a and 22b. By configuring the impedance measurement section as a pair of electrodes each having a shape resembling a comb as described above, it is possible to increase the strength of the electric field leaking from the comb-shaped planar electrodes 22a and 22b to the sample 5 to serve as a leaking electric field used for the measurement of the impedance. Thus, the impedance of a sample 5 can be measured with a high degree of precision even if the sample 5 has a small dielectric constant.

In addition, much like the property measurement apparatus according to the first embodiment of the present invention, in the property measurement apparatus according to the second embodiment of the present invention, the impedance measurement section almost does not have an effect on the flow of the sample 5. As a result, the property measurement apparatus according to the second embodiment of the present invention is also capable of measuring both the dynamic viscoelasticity and dielectric characteristic of a sample 5 in a wide range at the same time with a high degree of precision even if a sample 5 is a heterogeneous suspension liquid. The wide range covers samples 5 having any of viscosity coefficients ranging from a small viscosity coefficient to a large viscosity coefficient. A typical example of the sample 5 having a small viscosity coefficient is a liquid whereas a typical example of the sample 5 having a large viscosity coefficient is a gel-state substance.

It is to be noted that other possible configurations of the property measurement apparatus according to the second embodiment of the present invention and effects of the property measurement apparatus are the same as the property measurement apparatus according to the first embodiment which has been described before.

The present application contains subject matter related to that disclosed in Japanese Priority Patent Application JP 2008-140530 filed in the Japan Patent Office on May 29, 2008, the entire content of which is hereby incorporated by reference.

It should be understood by those skilled in the art that various modifications, combinations, sub-combinations and alterations may occur depending on design requirements and other factor in so far as they are within the scope of the appended claims or the equivalents thereof.

What is claimed is:

1. A method of property measurement comprising:
   inserting a sample between a first plate and a second plate;
   causing stress in the sample disposed between the first plate and the second plate;
   measuring a dynamic viscoelasticity of the sample based on the stress caused in the sample;
   applying a voltage between a first conductive layer and a second conductive layer of the second plate, the first conductive layer having a layer breaking gap within which a portion of the sample is disposed; and
   measuring a dielectric characteristic of the sample based on an impedance of the sample disposed in the layer breaking gap.

2. The method of claim 1, wherein measuring a dynamic viscoelasticity of the sample and measuring a dielectric characteristic of the sample occur at the same time.

3. The method of claim 1, wherein causing stress in the sample comprises actuating the first plate to cause distortion in the sample.

4. The method of claim 3, wherein actuating the first plate comprises rotating or vibrating the first plate.

5. The method of claim 1, wherein the sample disposed between the first plate and the second plate is a liquid.

6. The method of claim 1, wherein the sample disposed between the first plate and the second plate is a gel-state substance.

7. The method of claim 1, wherein measuring a dielectric characteristic of the sample based on an impedance of the sample disposed in the layer breaking gap comprises measuring an electrical signal passing through the layer breaking gap.

8. The method of claim 1, wherein measuring a dielectric characteristic of the sample based on an impedance of the sample disposed in the layer breaking gap comprises measuring a wave reflected by the layer breaking gap and a wave passing through the layer breaking gap.

9. The method of claim 1, wherein the first conductive layer comprises a pair of comb-shaped electrodes and the layer breaking gap comprises a gap separating the pair of comb-shaped electrodes.

10. A property measurement apparatus comprising:
    a first plate adapted to cause stress in a sample; and
    a second plate disposed opposite the first plate and having an impedance measurement section including an impedance analyzer, a network analyzer or a time-domain dielectric spectral instrument, the impedance measurement section further comprising:
      an insulation layer;
      a first conductive layer disposed adjacent the insulation layer and including a layer breaking gap; and
      a second conductive layer disposed adjacent the insulation layer on a side of the insulation layer opposite the first conductive layer.

11. The property measurement apparatus of claim 10, further comprising a rheometer configured to measure a dynamic viscoelasticity of the sample based on stress caused in the sample.

12. The property measurement apparatus of claim 11, wherein the impedance measurement section is configured to measure a dielectric characteristic of the sample when a portion of the sample is disposed in the layer breaking gap.

13. The property measurement apparatus of claim 12, wherein the rheometer is configured to measure the dynamic viscoelasticity of the sample at the same time that the impedance measurement section is configured to measure the dielectric characteristic of the sample.

14. The property measurement apparatus of claim 10, wherein the first plate is adapted to cause distortion in the sample.

15. The property measurement apparatus of claim 14, wherein the first plate is adapted to be rotated or vibrated so as to cause distortion in the sample.

16. The property measurement apparatus of claim 10, wherein the impedance measurement section is configured to measure a dielectric characteristic of the sample based on a measured impedance of the sample disposed in the layer breaking gap when a voltage is applied between the first conductive layer and the second conductive layer.

17. The property measurement apparatus of claim 10, wherein the first conductive layer comprises a pair of comb-shaped electrodes and the layer breaking gap comprises a gap separating the pair of comb-shaped electrodes.

18. The property measurement apparatus of claim 10, wherein a width of the layer breaking gap between conductive portions of the first conductive layer is between about 50 micrometers and 1000 micrometers.

* * * * *